United States Patent [19]

Okami et al.

[11] Patent Number: 4,870,172

[45] Date of Patent: Sep. 26, 1989

[54] BISUCABERIN

[75] Inventors: Yoshiro Okami; Shogo Kurasawa; Toshiyuki Kamayama, all of Tokyo; Atsushi Takahashi, Kawasaki; Masaaki Ishizuka, Tokyo; Hamao Umezawa, deceased, late of Tokyo, all of Japan, by Mieko Umezawa, Kazuo Umezawa, Yoji Umezawa, legal representatives

[73] Assignee: Microbial Chemistry Research Foundation, Tokyo, Japan

[21] Appl. No.: 74,369

[22] Filed: Jul. 16, 1987

[30] Foreign Application Priority Data

Jul. 22, 1986 [JP] Japan ................................ 61-170856

[51] Int. Cl.$^4$ ........................................ C07D 227/093
[52] U.S. Cl. .................................. 540/460; 435/121; 514/183
[58] Field of Search ......................................... 540/460

[56] References Cited

U.S. PATENT DOCUMENTS 4,174,428 11/1979 Tabushi et al. ..................... 540/460

Primary Examiner—Robert T. Bond
Attorney, Agent, or Firm—Frishauf, Holtz, Goodman & Woodward

[57] ABSTRACT

A novel compound having anti-tumor activity is disclosed which is 1,12-dihydroxy-1,6,12,17-tetraazacyclodocosan-2,5,13,16-tetrone produced microbiologically by culturing a microorganism belonging to the genus of Alteromonas or, in particular, *Alteromonas haloplanktis* SB-1123. The characterization data of the compound and the microbiological properties of the microorganism are described. The results of in vitro assays are given for the anti-tumor activity of the compound against L-1210 and IMC carcinoma cells.

1 Claim, 3 Drawing Sheets

BISUCABERIN

BACKGROUND OF THE INVENTION

The present invention relates to a novel compound of the chemical name 1,12-dihydroxy-1,6,12,17-tetraazacyclodocosan-2,5,13,16-tetrone called Bisucaberin having anti-tumor activity and a microbiological method for the preparation of the compound.

Needless to say, a variety of microorganisms produce so-called antibiotics and a large number of antibiotics have already been developed and used for medical purposes while a number of novel antibiotics are being added to the list of known antibiotics year by year. As a trend in recent years, a matter of concern in this field is to discover an antibiotic substance having anti-tumor activity and many reports in literatures are directed to this problem.

SUMMARY OF THE INVENTION

The inventors have continued extensive investigations to discover a novel compound having anti-tumor activity among the products of microorganisms and have discovered a novel compound to establish the present invention.

Thus, the present invention provides a novel compound having anti-tumor activity called Bisucaberin which is a 22-membered heterocyclic compound having a chemical name of 1,12-dihydroxy-1,6,12,17-tetraazacyclodocosan-2,5,13-16-tetrone and expressed by the structural formula:

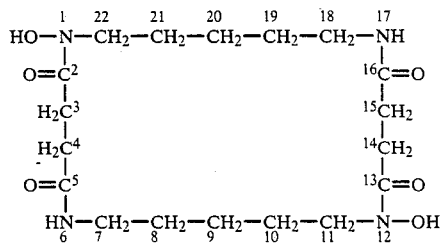

The above defined novel compound Bisucaberin is obtained as a microbiological product of a microorganism belonging to the genus of Alteromonas or, in particular, to the species of *Alteromonas haloplanktis*. A particularly productive strain of the microorganism has been isolated and deposited at an authentic organization for deposition of microorganisms.

DETAILED DESCRIPTION OF PREFERRED EMBODIMENTS

The inventive compound Bisucaberin expressed by the structural formula (I) given above is a novel compound not known in the prior art nor described in any publications. The compound is characterized by the following physical and chemical properties which establish the novelty of the compound.

(a) Appearance: colorless and crystalline
(b) Melting point: 190° C., with decomposition
(c) Ultraviolet absorption: $\lambda_{max}$ at 215 nm, $\epsilon=5740$ in methyl alcohol; and $\lambda_{max}$ at 215 nm, $\epsilon=5700$ in 0.1N-HCl/methyl alcohol solution
(d) Molecular weight: m/z=401 (MH$^-$) by SIMS (secondary ion mass spectrometry); and m/z=401 (MH$^+$) by EIMS (electron ion mass spectrometry)
(e) Molecular formula: $C_{18}H_{32}N_4O_6$
(f) Elementary analysis:

|  | C, % | H, % | N, % | O, % |
|---|---|---|---|---|
| Found | 53.69 | 7.97 | 13.20 | (25.14) |
| Calculated | 54.00 | 8.00 | 14.00 | 24.00 |

Figure 1:
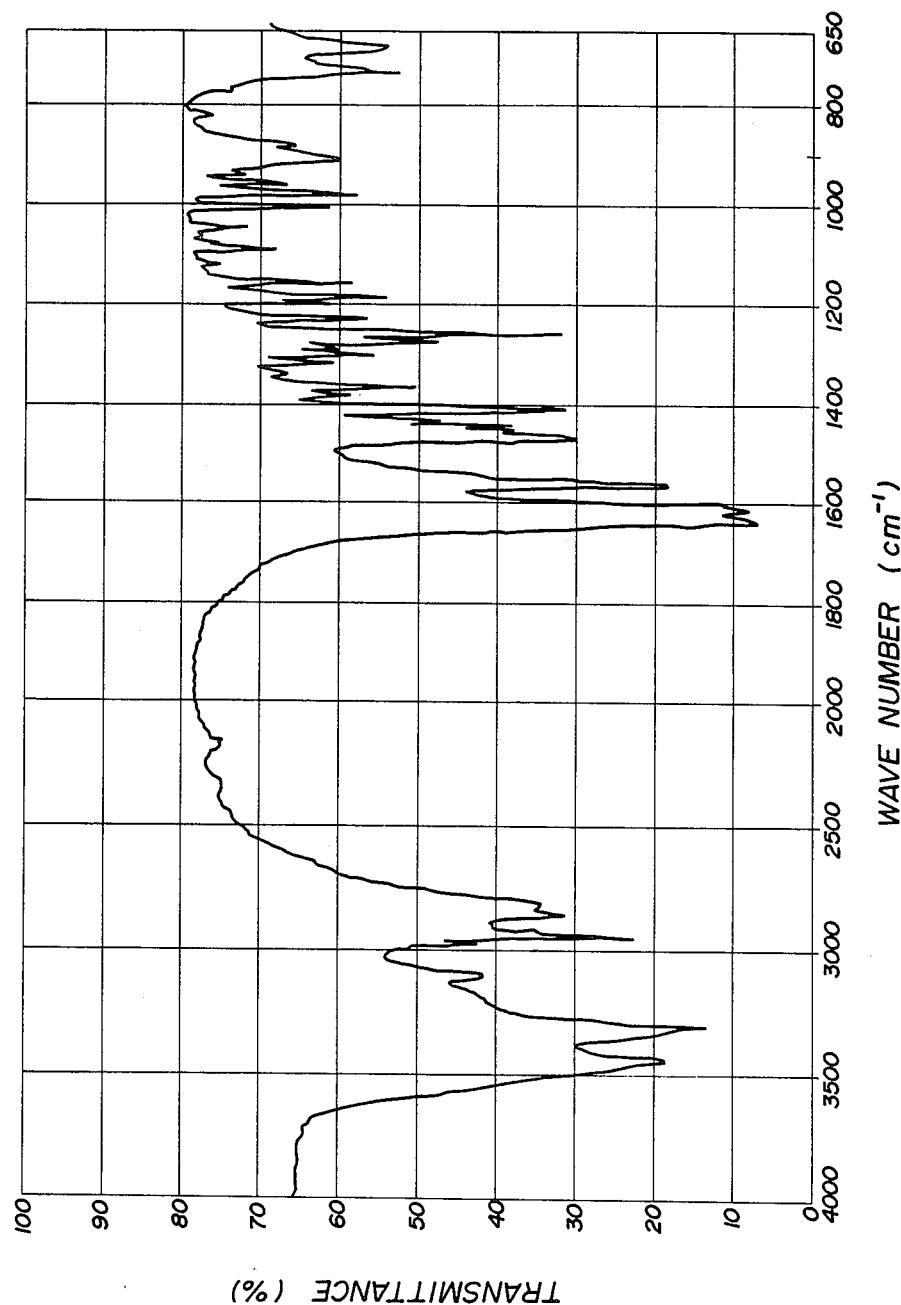
FIG. 1 is an infrared absorption spectrum of Bisucaberin.
Figure 2:
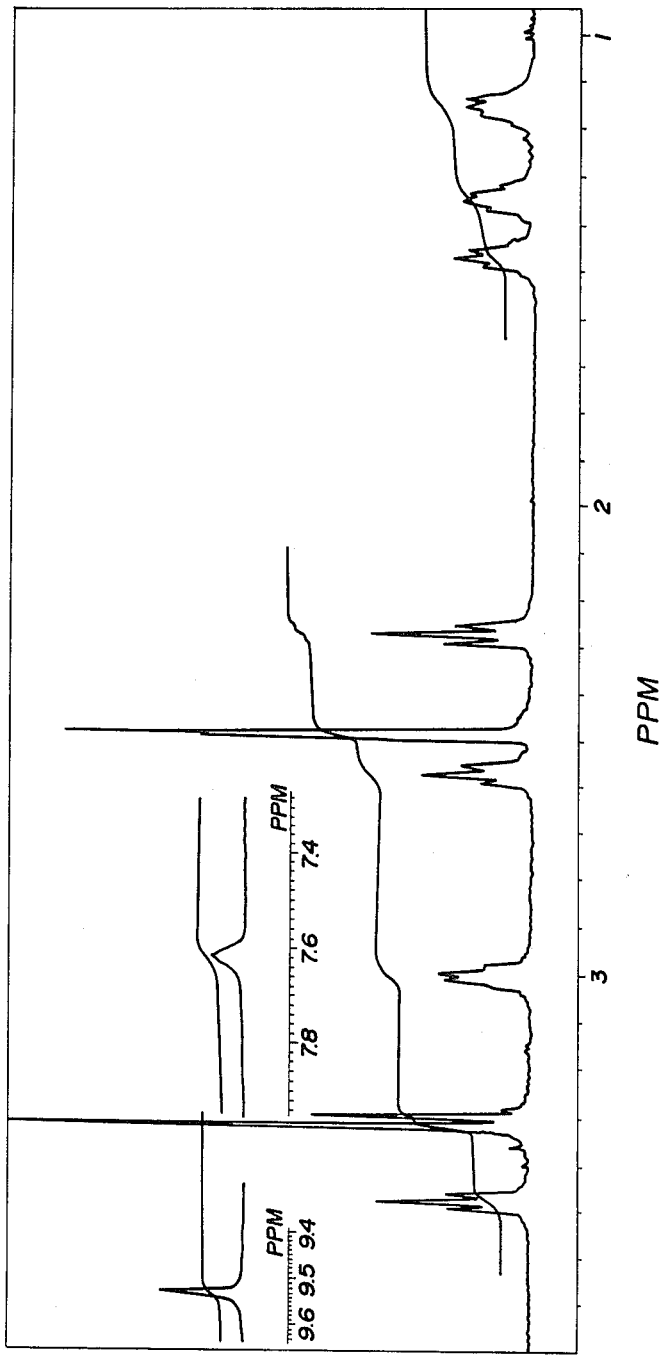
FIG. 2 is a proton NMR spectrum of Bisucaberin.
Figure 3:
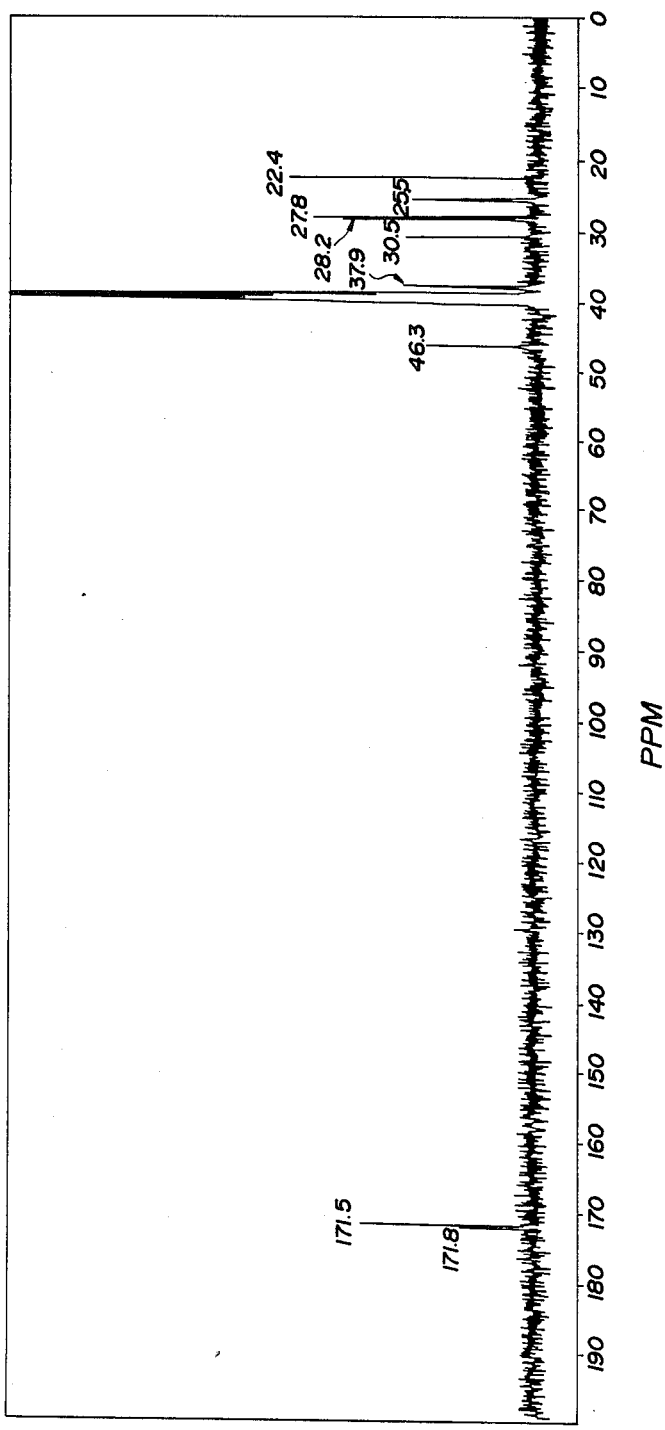
FIG. 3 is a $^{13}$C-NMR spectrum of Bisucaberin.

(g) Infrared absorption spectrum: (see FIG. 1)
(h) Proton NMR spectrum: (see FIG. 2—in d$_6$-DMSO, with
(h) $^{13}$C-NMR spectrum: (see FIG. 3—in d$_6$-DMSO, with reference to DMSO)
(i) Solubility behavior: soluble in dimethyl sulfoxide; slightly soluble in methyl alcohol; and hardly or not soluble in water
(j) Color reactions: positive in molybdenum-sulfuric acid reaction, tolidine reaction and ferric chloride reaction; and negative in ninhydrin reaction
(k) Thin-layer chromatography on silica gel (art 5715, Merck):
Rf=0.52 for chloroform:methyl alcohol (90:10); and
Rf=0.38 for chloroform:methyl alcohol (92:8)
(l) High-voltage paper electrophoresis (3000 volts, 20 minutes): Rm=0.0 for formic acid:acetic acid:water (1:3:36) given by the relative mobility taking the mobility of alanine as 1.0.

The inventive compound Bisucaberin characterized by the above given physical and chemical properties is found in the culture medium of a microorganism belonging to the genus of Alteromonas and capable of producing the compound so that the compound can be obtained by isolating from such a culture medium. A strain of the Alteromonas microorganisms capable of exhibiting particularly high productivity of Bisucaberin is *A. haloplanktis* SB-1123. This strain of the Alteromonas microorganism has been isolated by the inventors from the sea mud in the offing of Aomori Prefecture, Japan, and is characterized by the following microbiological properties.

(a) Morphology (1) Form and dimensions of cells: rod, 0.5–0.8 μm × 1.5–2.0 μm
(2) Motility: motile with polar flagella
(3) Spores: none
(4) Gram's stain: negative (b) Multiplication behavior in various culture media (1) Nutrient broth-agar plate culture: no multiplication
(2) Z medium-agar plate culture: medium multiplication, circular, flat to convex, entire, smooth, wet luminescence, translucent, light yellow (Z medium: sea water at a pH of 7.2 containing 0.5% of polypeptone and 0.1% yeast extract)
(3) Nutrient broth-agar slant culture: no multiplication
(4) Z medium-agar slant culture: medium multiplication, somewhat spreading, wet luminescence, butteriness, light yellow
(5) Nutrient broth liquid culture: no multiplication (6) Broth-sea water liquid culture: medium multiplication
(7) Broth-gelatin stab culture: no changes
(8) Broth-sea water-gelatin stab culture: liquefaction (c) Physiological properties (1) Reduction of nitrates: negative
(2) Denitrification reaction: negative
(3) MR test: negative
(4) VP test: negative
(5) Formation of hydrogen sulfide: negative
(6) Hydrolysis of starch: negative
(7) Formation of pigment: Water-soluble pigment not formed
(8) Oxidase: positive
(9) Catalase: positive
(10) Multiplication ranges
   Temperature: good multiplication in the range from 10° to 34° C., optimum temperature for multiplication in the range from 14° to 30° C., no multiplication at 4° C. and 39° C.
   pH: good multiplication in the range of pH 6 to 9
(11) Behavior to oxygen: aerobic
(12) O-F test by the Hugh & Leifson method: no acid formed
(13) Decarboxylase reaction: negative for lysine and negative for arginine
(14) Nutrient requirement: no multiplication in the absence of sea water or artificial sea water
(15) Assimilation of compounds

| D-Glucose | + | N—Acetyl glucosamine | + |
|---|---|---|---|
| D-Mannose | + | Succinic acid | + |
| D-Fructose | + | Fumaric acid | + |
| Saccharose | + | Citric acid | + |
| Maltose | + | Aconitic acid | − |
| Cellobiose | − | Erithritol | − |
| Melibiose | − | Mannitol | − |
| Lactose | − | Glycerol | − |
| L-Threonine | − | γ-Aminobutyric acid | − |
| L-Tyrosine | ± | D-Sorbitol | − |
| Putrescine | − | Maleic acid | − |
| Starch | ± | α-Ketoglutaric acid | − |
| Gluconic acid | − | | |

(16) Content of GC in DNA: 44.1%
The above described microbiological properties of the microorganism can be summarized as follows.
(1) The microorgansim is a marine bacterium.
(2) Multiplication thereof can take place only under aerobic conditions.
(3) The microorganism belongs to a class of Gram-negative bacilli.
(4) The microorganism has motility with polar flagella.
(5) The microorganism decomposes saccharides oxidatively and can assimilate saccharides.
(6) The content of GC in DNA is 44.1%.

According to the characterization described in Bergey's Manual of Systematic Bacteriology, volume 1 (1984), the above given characteristics well coincide with those of the microorganisms belonging to the genus of Alteromonas. This is the reason for the identification of the microorganism to be a bacterium belonging to the genus of Alteromonas.

The species to which the microorganism belongs can be determined from the important properties thereof including failure of multiplication at 4° C., utilizability of the compounds such as D-mannose, saccharose, maltose, N-acetylglucosamine, succinic acid, fumaric acid, cictric acid and the like as the carbon source, non-utilizability of the compounds such as erithritol, glycerol, sorbitol, maleic acid, α-ketoglutaric acid and the like as the carbon source, formation of no soluble pigments and so on. These characteristics indicate that the microorganism belongs to the species of *Alteromonas haloplanktis*. Although the non-utilizability of aconitic acid as the carbon source by this microorganism is inconsistent with the description in the above named manual, such a difference would not be sufficient to distinguish microbiological species from each other. Accordingly, it is concluded that the microorganism belongs to the species of *Alteromonas haloplanktis* (ZoBell and Upham 1944) Reichelt and Baumann 1973. The particular strain of the microorganism exhibiting the highest productivity of Bisucaberin is deposited and registered at Fermentation Research Institute, Agency of Industrial Science and Technology, Ministry of International Trade and Industry as *Alteromonas haloplanktis* SB-1123 under the Deposit No. FERM P-8803 (FERM BP-1360) and publicly available. It is of course that the microorganism used in the inventive method for the preparation of Bisucaberin is not limited to this particular strain but any variant of *Alteromonas haloplanktis* obtained by artificial or natural mutation of the strain can be used in the inventive method provided that the strain has the ability to produce Bisucaberin.

The above defined microorganism capable of producing Bisucaberin can be cultured by using a culture medium prepared by dissolving the requisite nutrients including carbon sources, nitrogen sources and inorganic ions with optional addition of vitamins, amino acids and the like in sea water which may be an artificial sea water. The compound as the carbon source is not particularly limitative and any of the compounds conventionally used in the culture of microorganisms can be used including, preferably, carbohydrates such as glucose, sucrose, starch, dextrin and the like. The nitrogen source material is also not particularly limitative and any of those conventionally used in the culture of microorganisms can be used including peptone, yeast extract, meat extract, corn steep liquor, soybean meal, casein, ammonium compounds and the like. It is preferable in order to enhance the efficiency of Bisucaberin production by the microorganism that the culture medium is prepared by using an artificial sea water containing a marine product such as a powder of cuttlefish and dried sardine which should preferably be a sardine of *Eugraulis japonica*.

The culture is performed preferably in a liquid culture medium under agitation and aeration. The temperature of culture should usually be in the range from 10° to 35° C. or, preferably, from 24° to 30° C. The culture should be continued until the desired Bisucaberin is accumulated in the liquid culture medium in a sufficiently high concentration. It is usual that a sufficiently high concentration of Bisucaberin is obtained by continuing the culture for 16 hours to 5 days.

Any known method is applicable to the recovery of Bisucaberin from the liquid culture medium containing the same. For example, a supernatant obtained by centrifugal separation of the liquid culture medium is passed through a bed of a synthetic adsorbent resin to have the active matter adsorbed thereon and then the eluted fraction containing the active matter is evaporated to precipitate a crystalline material which is further purified.

Bisucaberin provided by the present invention has an anti-tumor activity. For example, the compound is effective to enhance the activity of macrophages for cytolysis of cancer cells and to inhibit growth of cancer cells.

In the following, examples are given to illustrate the microbiological preparation of Bisucaberin as well as the anti-tumor activity of the compound in more detail.

EXAMPLE 1

Culture of *Alteromonas haloplanktis* SB-1123 (FERM BP-1360) was performed by inoculating the strain to 10 liters of a liquid culture medium having a pH of 7.2 and containing 2% by weight and 1% by weight of cuttlefish and dried sardine (*Engraulis japonica*) as milled in a half-strength artificial sea water (Jamarin S, a product by Jamarin Laboratory Inc.) which was shaken for 3 days at 27° C.

The liquid culture broth was then subjected to centrifugal separation to give a clear supernatant. A 7 liters portion of the supernatant was passed through a column containing 500 ml of an ion exchange resin (Diaion HP-20) and the resin bed was first washed with 5 liters of water and then eluted with 50:50 mixture of acetone and water to collect a fraction of 2 liters volume containing the active matter. The eluate solution of this fraction was evaporated under reduced pressure to precipitate a crude crystalline material which was washed first with acetone and then with ethyl acetate to give crystals of Bisucaberin in an amount of 2 g.

The crystalline Bisucaberin obtained in this manner was colored in brown due to impurities and could readily be purified into colorless, plate-like crystals of pure Bisucaberin by concentrating a fraction containing the compound obtained in the silica gel column chromatography using a 96:4 mixture of chloroform and methyl alcohol as the developer solvent.

EXAMPLE 2

The effect of Bisucaberin was examined on macrophage tumoricidal activity.

The macrophages were obtained from the peritoneal exudate cells derived by the injection of 10% proteosepeptone (Difco) to the peritoneal cavity of 8-weeks aged female C3H/HeN mice followed by the removal of the cells having no adhesion to plastics. The target cancer cells, the fibrosarcoma L-1023 induced in the C3H/HeN mouse with methyl cholanthrene, were labelled with tritiated thymidine. Culture of the cancer cells was performed in a RPMI 1640 culture medium at 37°0 C. in the presence of 5% carbon dioxide.

The assay was performed using a microplate of 96 wells, of which each well served to culture a blend of $2 \times 10^5$ cells of the macrophage and $1 \times 10^4$ cells of the target cancer cells with addition of an amount of Bisucaberin. The efficiency of the cytolysis was evaluated by determining the tritium in the supernatant of the culture medium released from the damaged cancer cells after 2 days of culture in the presence of a varied amount of Bisucaberin to give the results shown in Table 1 below. The activity of cytolysis was represented by the % cytolysis calculated by using the equation:

cytolysis, % = [(amount of experimental release) − (amount of spontaneous release)]/[(amount of maximum release) − (amount of spontaneous release)].

in which (amount of spontaneous release) was the value when no macrophage was added to the culture and (amount of maximum release) was the value when 0.5% SDS was added in place of the macrophage.

TABLE 1

| Concentration, final, of Bisucaberin added, μg/ml | Cytolysis, % | | |
|---|---|---|---|
| | + Macrophage, % | | − Macrophage, % |
| 67 | 38.6 | 41.5 | 15.3 |
| 33 | 64.8 | 71.8 | 12.0 |
| 11 | 45.7 | 47.1 | 6.5 |
| 3.6 | 13.3 | 14.8 | 0.3 |
| 1.2 | 2.8 | — | — |
| 0 | 0 | — | 0 |

EXAMPLE 3

Assay was performed to examine the activity of Bisucaberin for the inhibition of the growth of mouse leukemia cells L-1210 and mouse IMC carcinoma cells. The conditions of experiment were as follows.

(1) Tumor cells (a) L-1210: cultured in passage in a MEM culture medium containing 10% calf serum
(b) IMC carcinoma: cultured in passage in a RPMI 1640 culture medium containing 10% fetal bovine serum.

Each culture was started in the preceding day of the assay which was performed by using the tumor cells at the stage of exponential growth.

(2) Sample

Bisucaberin was dissolved in dimethyl sulfoxide in a volume corresponding to 10% of the final solution with addition of 5 μl of a detergent (Tween 80) followed by adjustment of the concentration to 2 mg/ml with a MEM culture medium. This master solution was diluted successively in six times of each 4 fold dilution with the same culture medium.

(3) Method of assay (a) A microplate of 96 wells was used and each 10 μl portion of the sample solution was introduced into 3 wells per one of the test specimens.
(b) The tumor cells were suspended in the respective media for passage culture in a density of $1 \times 10^5$ cells per ml and a 0.2 ml portion of the cell suspension was added to each well.
(c) After 48 hours of culture at 37° C. in a carbon dioxide incubator, a 0.1 ml volume of the cell suspension was taken and diluted 100 times with ISOTON II or a physiological saline solution. The number of cells in this diluted cell suspension was counted using a Coulter Counter.
(d) The value of % inhibition of the cell growth was calculated for each dilution of the sample solution by making comparison with the control to give the results shown in Table 2.

TABLE 2

| Tumor cell | Concentration of Bisucaberin, μg/ml | Number of cells | Inhibition of cell growth % |
|---|---|---|---|
| L-1210 | 0 (control) | 2888 ± 106 | — |
| | 100.0 | 429 ± 47 | 85 |

TABLE 2-continued

| Tumor cell | Concentration of Bisucaberin, μg/ml | Number of cells | Inhibition of cell growth % |
|---|---|---|---|
| | 25.0 | 425 ± 3 | 85 |
| | 6.25 | 908 ± 11 | 69 |
| | 1.56 | 2428 ± 100 | 16 |
| | 0.39 | 2727 ± 151 | 6 |
| IMC carcinoma | 0 (control) | 3910 ± 96 | — |
| | 100.0 | 557 ± 26 | 86 |
| | 25.0 | 547 ± 16 | 86 |
| | 6.25 | 1712 ± 24 | 56 |
| | 1.56 | 3374 ± 44 | 14 |
| | 0.39 | 3602 ± 2 | 8 |

The values of the % inhibition shown in Table 2 were plotted on graph for each type of the tumor cells to prepare a curve of Bisucaberin concentration vs. % inhibition, from which the concentration of Bisucaberin corresponding to 50% inhibition, $IC_{50}$, was determined by interpolation. The values of $IC_{50}$ were 3.9 μg/ml and 5.1 μg/ml for L-1210 and IMC carcinoma, respectively.

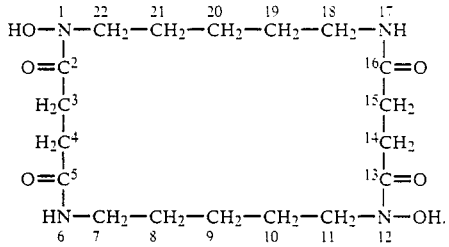

What is claimed is:

1. Bisucaberin, which is a 1,12-dihydroxy-1,6,12,17-tetraazacyclodocosan-2,5,13,15-tetrone expressed by the structural formula